United States Patent [19]
Imura et al.

[11] Patent Number: 5,636,015
[45] Date of Patent: Jun. 3, 1997

[54] MEASURING APPARATUS FOR MEASURING AN OPTICAL PROPERTY OF A FLUORESCENT SAMPLE

[75] Inventors: Kenji Imura, Toyohashi; Kiyoshi Imai, Toyokawa, both of Japan; Tokihisa Kawabata, Hamburg, Germany; Masayuki Makino, Aichi-ken, Japan

[73] Assignee: Minolta Co., Ltd., Osaka, Japan

[21] Appl. No.: 648,335

[22] Filed: May 15, 1996

[30] Foreign Application Priority Data

May 17, 1995 [JP] Japan ................................ 7-118724

[51] Int. Cl.$^6$ ........................................ G01J 3/00
[52] U.S. Cl. .................... 356/72; 356/319; 250/461.1
[58] Field of Search ....................... 356/72, 73, 319, 356/326, 328, 317, 318; 250/461.1

[56] References Cited

U.S. PATENT DOCUMENTS 4,699,510  10/1987  Alguard ................................ 356/73
5,384,641  1/1995  Imura ................................ 356/446

OTHER PUBLICATIONS

Rolf Griesser, "Assessment of Whiteness and Tint of Fluorescent Substrates with Good Interinstrument Correlation," *Color Research and Application*, vol. 19, No. 6, Dec. 1994, pp. 446–460.

J. Anthony Bristow, "The Calibration of Instruments for the Measurement of Paper Whiteness," *Color Research and Application*, vol. 19, No. 6, Dec. 1994, pp. 475–483.

Japanese Industrial Standard, JIS Z 8717—1989, "Methods of Measurement for Colour of Fluorescent Objects."

*Primary Examiner*—F. L. Evans
*Attorney, Agent, or Firm*—Burns, Doane, Swecker & Mathis, LLP

[57] ABSTRACT

The measuring apparatus of the present invention measures the optical properties of a sample containing a fluorescent material by irradiating the sample with light containing a UV component. In the present invention are provided a first light source for irradiating the sample with light containing a UV component, a second light source for irradiating the sample with light which does not contain a UV component, light receiving element for receiving light reflected from the sample irradiated by said light sources, and output means for generating weighting coefficients for weighting the output of the light receiving element during emission by each light source. The optical properties of the sample is calculated based on the output of the light receiving element for a first light source, output of the light receiving element for a second light source, and the respective weighting coefficients. Accordingly, measurement values can be obtained which are equal to values when measurement is accomplished with a standard light source.

23 Claims, 4 Drawing Sheets

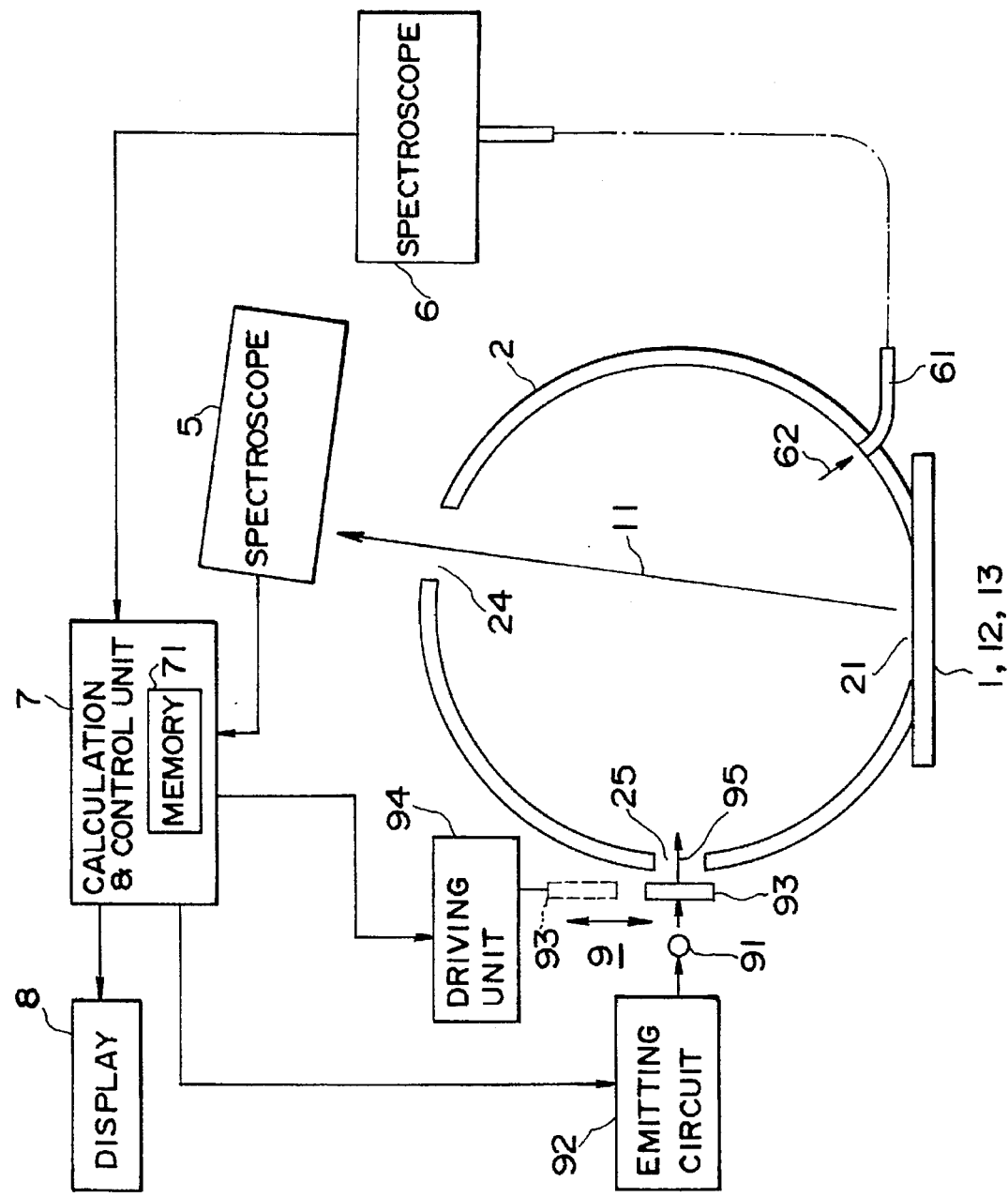

MEASURING APPARATUS FOR MEASURING AN OPTICAL PROPERTY OF A FLUORESCENT SAMPLE

BACKGROUND OF THE INVENTION

1. Field of the Invention

The present invention relates to an apparatus for measuring an optical property of a sample, and specifically relates to an apparatus for measuring an optical property of a sample containing fluorescent material.

2. Description of the Related Art

Generally, when a measurement sample containing fluorescent material (hereinafter referred to as "fluorescent sample") is irradiated by white light I, the visual characteristics are expressed by the total spectral radiant factor $\beta_{t,I}(\lambda)$. Total spectral radiant factor $\beta_{t,I}(\lambda)$ is the ratio of spectral radiance illuminated and observed under the same conditions at wavelength $\lambda$ of a complete diffuse reflection surface and an observed fluorescent sample, or otherwise the ratio of the flux intensity at wavelength $\lambda$ reflected from the complete diffuse reflection surface and fluorescent sample in the same solid angle of the same direction when illuminated under the same conditions, and is expressed by Equation 1.

$$\beta_{t,I}(\lambda) = S(\lambda)/S_0(\lambda) \tag{1}$$

In this equation, $S(\lambda)$ is the intensity at wavelength $\lambda$ of the radiant light from the fluorescent sample, and $S_0(\lambda)$ is the intensity at wavelength $\lambda$ of the radiant light reflected from the complete diffuse reflection surface.

The total spectral radiant factor $\beta_{t,I}(\lambda)$ is expressed by Equation 2 when the reflecting spectral radiance factor of the reflected light component of a fluorescent sample is expressed as $\beta_{o,I}(\lambda)$, and the fluorescent spectral radiance factor of the fluorescent light component reflected from a fluorescent sample is expressed as $\beta_{f,I}(\lambda)$.

$$\beta_{t,I}(\lambda) = \beta_{o,I}(\lambda) + \beta_{f,I}(\lambda) \tag{2}$$

The fluorescent spectral radiance factor $\beta_{f,I}(\lambda)$ is the ratio of the intensity at wavelength $\lambda$ of the fluorescent light component reflected by a fluorescent sample illuminated by ultraviolet light (hereinafter referred to as "UV light") and the intensity at wavelength $\lambda$ of the flux reflected by the complete diffuse reflection surface under the same illumination conditions, and is expressed by Equation 3.

$$\beta_{f,I}(\lambda) = \int_{uv} i_I(\lambda') e(\lambda,\lambda') d\lambda' / S_0(\lambda) \tag{3}$$

The symbol $i_I(\lambda)$ refers to the spectral intensity of the illumination light, the symbol $e(\lambda,\lambda')$ refers to the efficiency of radiant fluorescent light at wavelength $\lambda$ excited by illumination at wavelength $\lambda'$ of a fluorescent sample, and symbol $S_o(\lambda)$ refers to the intensity at wavelength $\lambda$ of the reflected light from a complete diffuse reflecting surface via illumination light under the same conditions.

The fluorescent spectral radiance factor $\beta_{f,I}(\lambda)$ differs from the reflecting spectral radiance factor $\beta_{o,I}(\lambda)$, and depends on the spectral distribution of the illumination light due to the correlation of the intensity of the UV component within the illumination light to the radiance factor at wavelength $\lambda$.

In the following discussion, the appended letter I used in the symbols expresses the type of white light, the appended letter D expresses the standardized D65 illuminant of the International Commission on Illumination (CIE) measuring system, and the appended letter X refers to illumination by a light source.

Although standard light D65 is typically used in evaluating fluorescent samples, the same fluorescent sample may produce a difference between the $\beta_{f,D}(\lambda)$ and $\beta_{f,X}(\lambda)$ in Eq. 3 if there is a difference between the spectral intensity $i_D(\lambda)$ of the D65 illuminant and the spectral intensity $i_x(\lambda)$ of the normal illumination light. As a result, a difference arises between $\beta_{t,D}(\lambda)$ and $\beta_{t,x}(\lambda)$ of Eq. 2.

Heretofore, a method is used for reconciling the spectral intensity $i_x(\lambda)$ to the spectral intensity $i_D(\lambda)$ by adjusting the intensity of the UV component within the illumination light ("Assessment of Whiteness and Tint of Fluorescent Substrates with Good Interinstrument Correlation," Rolf Griesser; "The Calibration of Instruments for the Measurement of Paper Whiteness," J. Anthony Bristow, Color Research and Application, Vol.19 No.6, December, 1994).

FIG. 4 is an illustration showing the construction of this conventional spectrophotometer; UV intensity is adjusted by inserting a UV cut filter capable of adjusting the degree of insertion in the flux of the illumination light to eliminate the UV component from part of the illumination flux. Equation 3 is expressed by Equations 4 in this situation.

$$\beta_{f,x}(\lambda) = \int_{uv} a \cdot i_x(\lambda') e(\lambda,\lambda') d\lambda' / S_0(\lambda) \tag{4}$$

In Eq. 4, the letter "a" refers to the attenuation of the UV component.

In FIG. 4, fluorescent sample 1 is arranged at a sample aperture 21 of integrating sphere 2. Light source 101 driven by an emitting circuit 104 includes sufficient UV component and comprises a xenon lamp; light flux 102 passes through aperture 23 and enters integrating sphere 2. A UV cut filter 103 is inserted so as to partially block the optical path of flux 102, and the flux which passes through the UV cut filter 103 has the UV component eliminated. The degree of insertion of the UV cut filter 103 is adjustable so as to allow adjustment of the UV intensity in the illumination light.

Flux 102 entering integrating sphere 2 undergoes diffuse reflection within the sphere and forms diffuse light which illuminates the fluorescent sample 1, and the radiant light 11 reflected in a predetermined direction from the illuminated surface passes through observation aperture 24 and enters sample spectral unit 5 which detects the spectral intensity. Similarly, light flux 62 having the same intensity as the illumination light of fluorescent sample 1 enters the monitoring optical fiber 61 so as to be directed to monitoring spectral unit 6 which detects the spectral intensity.

A nonfluorescent standard white light panel 12 having known spectral reflectance is arranged at aperture 21 of integrating sphere 2 to detect the spectral intensity of the illuminant of nonfluorescent standard white panel 12 and the spectral intensity of the radiant light 11 reflected from said nonfluorescent standard white panel 12.

Calculation and control unit 70 calculates the total spectral radiant factor $\beta_{t,X}(\lambda)$ from the spectral intensity data input from spectroscopes 5 and 6 and based on Equation 5.

$$\beta_{t,x}(\lambda) = W(\lambda) \frac{S(\lambda)}{R(\lambda)} / \frac{S_W(\lambda)}{R_W(\lambda)} \quad \text{Eq. 5}$$

In the equation, $W(\lambda)$ refers to the well-known spectral reflectance of the nonfluorescent standard white panel 12, $S_W(\lambda)$ refers to the spectral intensity of the radiant light reflected from the nonfluorescent standard white panel 12, $R_W(\lambda)$ refers to the spectral intensity of the illuminant of nonfluorescent standard white panel 12, $S(\lambda)$ refers to the spectral intensity of the radiant light reflected from the fluorescent sample 1, and $R(\lambda)$ refers to the spectral intensity of the illuminant of fluorescent sample 1.

A standard sample containing fluorescent material (hereinafter referred to as "standardized fluorescent sample") 13 is used to determine the degree of insertion of UV cut filter 103, i.e., to correct the UV intensity by determining the attenuation "a" of the UV component in Eq. 4. Standardized fluorescent sample 13 comprises paper, plastic, cloth or the like having a predetermined index of CIE whiteness under standard D65 illuminant, e.g., exhibits a degree of CIE whiteness under standard D65 illuminant when a paper is used as a standardized fluorescent sample.

The standardized fluorescent sample 13 is measured using a spectrophotometer shown in FIG. 4, and the UV intensity is corrected by adjusting the degree of insertion of UV cut filter 103 so as to match the value of CIE whiteness calculated from the obtained total spectral radiant factor $\beta_{t,X}(\lambda)$ to the predetermined index of CIE whiteness.

If the adjusted UV cut filter 103 is inserted and the fluorescent sample 1 is measured when the fluorescent material contained in said sample is identical to or similar to the fluorescent material contained in the standardized fluorescent sample used to correct UV intensity, i.e., when the $e(\lambda, \lambda')$ in Eq. 3 are identical or similar, the measured CIE whiteness closely approaches the CIE whiteness when fluorescent sample 1 is illuminated by standard D65 illuminant.

A second conventional example is a method for determining the total spectral radiance factor of a fluorescent sample, and is the total spectral radiance factor synthesis method described in JIS Z 8717. This method uses n individual light sources $i_k(\lambda)$ (where $k=1, 2, \ldots, n$) having different spectral intensities. First, $a_k$ is determined so that the value of Eq. 6 approaches the spectral intensity $i_D(\lambda)$ of standard D65 illuminant. Next, the total spectral radiant factor $\beta_{t,X}(\lambda)$ is synthesized from the total spectral radiant factor $\beta_{t,k}(\lambda)$ of the fluorescent sample illuminated by each light source via Eq. 7.

$$\sum_{k=1}^{n} a_k \cdot i_k(\lambda) \qquad \text{Eq. 6}$$

$$\beta_{t,x}(\lambda) = \sum_{k=1}^{n} a_k \cdot \beta_{t,k}(\lambda) \qquad \text{Eq. 7}$$

This method synthesizes each light source such that the spectral intensity approaches standard D65 illuminant, and can produce a total spectral radiance factor equal to standard D65 illuminant without requiring a standard fluorescent sample as in conventional art irrespective of the kind of composite material of the fluorescent sample.

In the conventional art shown in FIG. 4, time is required for measurement because measurement operation and UV cut filter movement must be repeated for adjustment of the degree of insertion of UV cut filter 103. As previously described, since UV intensity is corrected relative to a predetermined index of a standardized fluorescent sample such as CIE whiteness, the total spectral radiance factor $\beta t, X(\lambda)$ may match the total spectral radiance factor $\beta t, D(\lambda)$ under standard D65 illuminant at the predetermined index. However, those factors may not necessarily match each other at another index. Accordingly, other indexes calculated from the total spectral radiance factor may result in, for example, nonmatching color values.

The second example of conventional art requires the provision of many light sources having different spectral intensities to closely approach the standard D65 illuminant, and is impractical due to the complex construction and high cost.

SUMMARY OF THE INVENTION

An object of the present invention is to eliminate the previously described problems by providing a measuring apparatus for measuring an optical property of a sample containing fluorescent material, said measuring apparatus having a simple construction and being capable of quickly and accurately producing optical properties equal to optical properties under standard illumination.

A measuring apparatus of the present invention comprises a first light source for irradiating the sample with a light including ultraviolet rays, a second light source for irradiating the sample with a light not including ultraviolet rays, a light receiving element for receiving a light from the sample irradiated by said first or second light source, and an output means for outputting weighting coefficients for weighting the output of said light receiving element during illumination by each light source. The optical properties of a sample are calculated based on the output of the light receiving element during emission by said first light source, the output of the light receiving element during emission by said second light source, and said weighting coefficients.

A measuring apparatus of the present invention comprises a light source for irradiating the sample with a light including ultraviolet rays, a UV cut member movable between a first position and a second position, wherein said UV cut member allows the ultraviolet rays of said light source to irradiate the sample at the first position and prevents the ultraviolet rays from irradiating the sample at the second position, a light receiving element for receiving light from the sample irradiated by said light source, and output means for outputting weighting coefficients for weighting the output of the light receiving element when the UV cut member is at the first position and the output of said light receiving member when the UV cut member is at the second position. The optical properties of the sample are calculated based on the output of the light receiving element when the UV cut member is at the first position, the output of the light receiving element when the UV cut member is at the second position, and the weighting coefficients.

A measuring method of the present invention comprises the steps of irradiating the sample with a first light including ultraviolet rays and receiving a light from the sample irradiated by the first light, irradiating the sample with a second light, wherein the ratio of ultraviolet rays of the second light is different from that of said first light and receiving a light from the sample irradiated by the second light, generating weighting coefficients which weight the light reception output during emission by each light source, and calculating an optical property of the sample based on the output of the light receiving element during emission by the first and second light sources, and the respective weighting coefficients.

According to the present invention, measurement values are obtained which are equal to values obtained when measuring with a standard light source by using weighting coefficients to suitably weight the measurement value obtained via illumination light containing UV rays, and the measurement value obtained via illumination light not containing UV rays. Thus, it is not necessary to adjust the degree of insertion of the UV cut filter and is not necessary to provide many light sources having different spectral intensities. Furthermore, the optical properties of a sample containing fluorescent material can be measured accurately and quickly by means of a simple construction.

Other objects and advantages of the present invention will become apparent from the detailed description to follow taken in conjunction with the appended claims.

BRIEF DESCRIPTION OF THE DRAWINGS

FIG. 3 shows the construction of a measuring device of a second embodiment of the present invention;

DETAILED DESCRIPTION OF THE PREFERRED EMBODIMENTS

Figure 1:
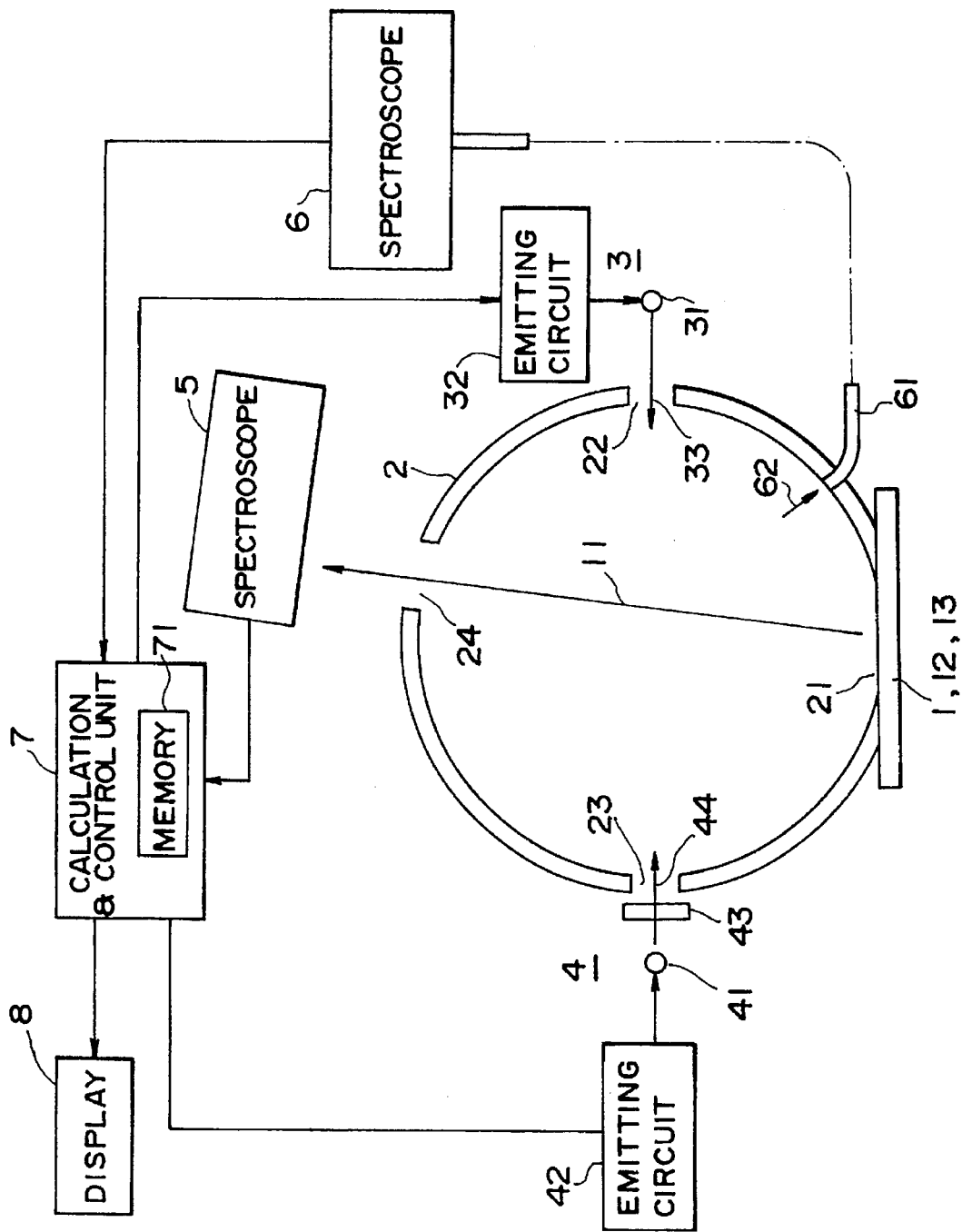
FIG. 1 illustrates the construction of a first embodiment of the measuring apparatus of the present invention.

FIG. 1 shows the construction of the spectrophotometer of a first embodiment of the present invention.

Integrating sphere 2 is coated on its interior wall with a white diffuse reflection coating such as MgO, BaSO$_4$ or the like, so as to generate diffuse light by mixing the entering light flux, and at suitable locations is provided with a sample aperture 21, light source apertures 22 and 23, and observation aperture 24, and is further provided with a first light source unit 3 and second light source unit 4 near apertures 22 and 23, respectively. Fluorescent sample 1 is positioned at sample aperture 21 of integrating sphere 2.

First light source unit 3 comprises a lamp 31 and emitting circuit 32. Lamp 31 emits light flux containing a UV component such as a xenon lamp, and is disposed at light source aperture 22 of integrating sphere 2. Emitting circuit 32 pulses to drive lamp 31, such that the pulse light flux passes through aperture 22 and enters integrating sphere 2.

Second light source unit 4 comprises an emitting circuit 42 and UV cut filter 43. Lamp 41 may be, for example, a xenon lamp, and is disposed at light source aperture 23 of integrating sphere 2. UV cut filter 43 is interposed between lamp 41 and light source aperture 23, and blocks the UV component, for example, at wavelengths less than 40 nm. Emitting circuit 42 pulses to drive lamp 41, such that pulse light flux 44 passes through UV cut filter 43 which removes the UV component therefrom and enters integrating sphere 2.

Light fluxes 33 and 44 in integrating sphere 2 undergo diffuse reflection by the interior wall and become producing a diffuse light which illuminates fluorescent sample 1, and radiant light 11 reflected from the illuminated fluorescent sample 1 in a predetermined direction comes out from integrating sphere 2 via observation aperture 24.

A spectroscope 5 is provided at observation aperture 24 of integrating sphere 2. Spectroscope 5 detects the spectral intensity of radiant light 11, and the obtained spectral intensity data are transmitted to a calculation and control unit 7 described later.

The input tip of optical fiber 61 is arranged adjacent to sample aperture 21 of integrating sphere 2. The output tip of optical fiber 61 is connected to spectroscope 6, and the monitor light flux 62 having a spectral distribution identical to the illumination light of fluorescent sample 1 entering the input tip is directed by optical fiber 61 to spectroscope 6. Spectroscope 6 monitors the illumination light by detecting the spectral intensity of the monitor light flux 62, and the obtained spectral intensity data are transmitted to calculation and control unit 7.

Calculation and control unit 7 controls the actuation of emitting circuits 32 and 42, and controls the lighting of lamps 31 and 41, and calculates total spectral radiant factor $\beta_{t,x}(\lambda)$ via a sequence described later. A memory 71 is provided for storing data such as spectral intensity data obtained by spectroscopes 5 and 6. Display 8 comprises, for example, a CRT, liquid crystal or the like, and displays calculation results such as the total spectral radiance factor and the like calculated by calculation and control unit 7.

Calculation and control unit 7 may also calculate other index values such as color values and the like from the aforesaid calculated total spectral radiance factor $\beta_{t,x}(\lambda)$.

The sequence for measuring fluorescent sample 1 and calculating total spectral radiance factor $\beta_{t,x}(\lambda)$ is described hereinafter.

First the reflectivity is corrected using nonfluorescent standard white panel 12 which does not contain any fluorescent material.

That is, a nonfluorescent standard white panel 12 having a known spectral reflectivity $W(\lambda)$ is arranged at sample aperture 21, lamp 31 is turned ON, and the spectral intensities $S_{W1}(\lambda)$ of the radiant light 11 reflected from nonfluorescent standard white panel 12 and $R_{W1}(\lambda)$ of the monitor light flux 62 are detected, and stored in memory 71. Then, lamp 41 is turned ON, and the spectral intensities $S_{W2}(\lambda)$ of the radiant light 11 reflected from nonfluorescent standard white panel 12 and $R_{W2}(\lambda)$ of the monitor light flux 62 are detected, and stored in memory 71.

Next, UV intensity is corrected using a standardized fluorescent sample 13 having a known total spectral radiance factor $\beta_{t,D}(\lambda)$ illuminated by a standard D65 luminant.

That is, a standardized fluorescent sample 13 is arranged at sample aperture 21, lamp 31 is turned ON, and the spectral intensities $S_1(\lambda)$ of the radiant light 11 from the standardized fluorescent sample 13 and $R_1(\lambda)$ of monitor flux 62 are detected and stored in memory 71. Then, lamp 41 is turned ON, and the spectral intensities $S_2(\lambda)$ of the radiant light 11 from the standardized fluorescent sample 13 and $R_2(\lambda)$ of monitor flux 62 are detected and stored in memory 71.

When the weighting coefficients $a_1(\lambda)$ and $a_2(\lambda)$ (where $a_1(\lambda)+a_2(\lambda)=1$) are applied, said weighting coefficients $a_1(\lambda)$ and $a_2(\lambda)$ are calculated for each wavelength so that the total spectral radiance factor $\beta_{t,x}(\lambda)$ calculated via Eq. 8 using the various data, e.g., $S_{W1}(\lambda)$, $R_{W1}(\lambda)$, $S_{W2}(\lambda)$, $R_{W2}(\lambda)$, $S_1(\lambda)$, $R_1(\lambda)$, $S_2(\lambda)$, $R_2(\lambda)$, of the spectral intensities stored in memory 71 are equal to the known total spectral radiance factor $\beta_{t,D}(\lambda)$ of the standardized fluorescent sample 13. Thus, the UV intensity is corrected.

$$\beta_{t,x}(\lambda) = W(\lambda) \frac{S'(\lambda)}{R'(\lambda)} \Big/ \frac{Sw'(\lambda)}{Rw'(\lambda)} \qquad \text{Eq. 8}$$

$S'(\lambda)=a1(\lambda)\cdot S1(\lambda)+a2(\lambda)\cdot S2(\lambda)$ $R'(\lambda)=a1(\lambda)\cdot R1(\lambda)+a2(\lambda)\cdot R2(\lambda)$ $Sw'(\lambda)=a1(\lambda)\cdot Sw1(\lambda)+a2(\lambda)\cdot Sw2(\lambda)$ $Rw'(\lambda)=a1(\lambda)\cdot Rw1(\lambda)+a2(\lambda)\cdot RW2(\lambda)$ Thus, the light flux 33 containing a UV component from first light source 3, and light flux 44 which does not contain a UV component from second light source 4 are weighted by weighting coefficients $a_1(\lambda)$ and $a_2(\lambda)$, respectively, to synthesize a composite light source under the illumination of which the total spectral radiance factor $\beta_{t,x}(\lambda)$ matches at every wavelength to the known total spectral radiance factor $\beta_{t,D}(\lambda)$ under illumination by a standard D65 illuminant.

In the case of the nonfluorescent standard white panel, $S_{W1}(\lambda)/R_{W1}(\lambda)$ and $S_{W2}(\lambda)/R_{W2}(\lambda)$ may be equal, and $S_{W}(\lambda)$ and $R_{W}'(\lambda)$ of Eq. 8 may be substituted for $S_{W1}(\lambda)/R_{W1}(\lambda)$, or $S_{W2}(\lambda)/R_{W2}(\lambda)$. Pursuant to the aforesaid construction, the first and second light source unit 3 and 4 may be at different positions with different monitoring characteristics, preferably calculated by Eq. 8.

Figure 4:
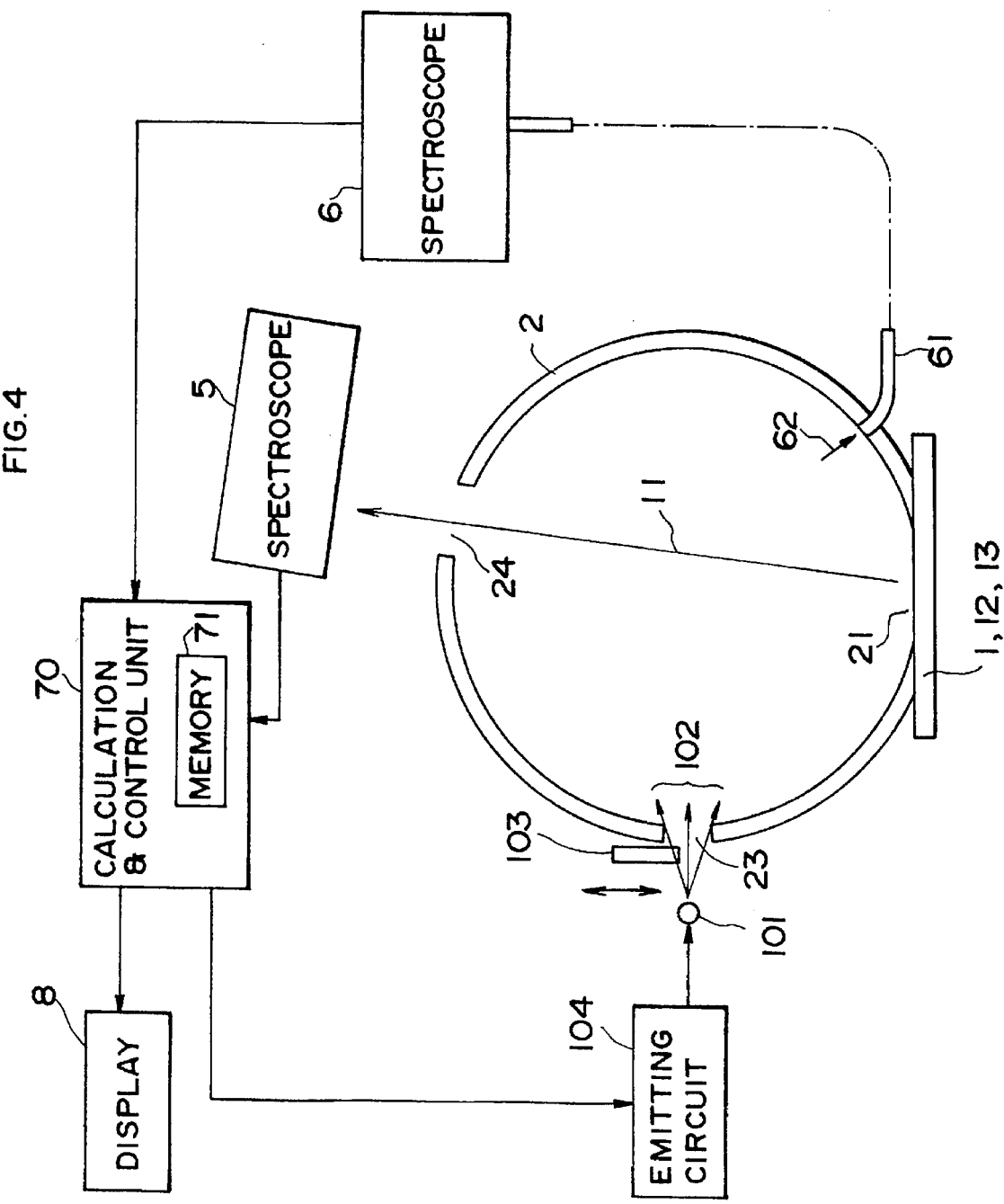
FIG. 4 shows the construction of a conventional measuring device.

As shown in FIG. 4, the conventional art determines the fluorescent spectral radiance factor $\beta_{f,x}(\lambda)$ at each wavelength by using the attenuation "a" of the light flux of the UV component flatly for all wavelengths $\lambda$ of the visible range.

In contrast, in the present embodiment, the weighting coefficient, i.e., the attenuation coefficient $a(\lambda)$, is suitably set for each wavelength $\lambda$ in the visible range such that the fluorescent spectral radiance factor $\beta_{f,x}(\lambda)$ and total spectral radiance factor $\beta_{t,x}(\lambda)$ are equal at every wavelength $\lambda$ to the fluorescent spectral radiance factor $\beta_{f,D}(\lambda)$ and total spectral radiance factor $\beta_{t,D}(\lambda)$ under standard D65 illumination, as shown in Eq. 9. Accordingly, the total spectral radiance factor $\beta_{t,x}(\lambda)$ has high accuracy throughout the entire wavelength range.

$$\beta_{f,x}(\lambda) = \int_{uv} a(\lambda) \cdot i_x(\lambda') e(\lambda,\lambda') d\lambda' / S_0(\pi) \qquad \text{Eq. 9}$$

UV intensity is corrected as described above, and the weighting coefficients $a_1(\lambda)$ and $a_2(\lambda)$ are calculated at each wavelength, whereupon fluorescent sample 1 is measured.

First, fluorescent sample 1 is disposed at sample aperture 21, lamp 31 is turned ON, and the spectral intensities $S_1(\lambda)$ of the radiant light 11 from fluorescent sample 1 and $R_1(\lambda)$ of monitor light flux 62 are detected, and stored in memory 71. Then, lamp 41 is turned ON, and the spectral intensities $S_2(\lambda)$ of the radiant light 11 from fluorescent sample 1 and $R_2(\lambda)$ of monitor light flux 62 are detected and stored in memory 71.

Next, the weighting coefficients $a1(\lambda)$ and $a2(\lambda)$ calculated by the UV intensity correction are used to calculate the total spectral radiance factor $\beta_{t,x}(\lambda)$ based on Eq. 8.

The calculated total spectral radiance factor $\beta_{t,x}(\lambda)$ is a value equal to the total spectral radiance factor $\beta_{t,D}(\lambda)$ under standard D65 illumination when fluorescent sample 1 and the fluorescent material of standardized fluorescent sample 13 used for UV intensity correction are identical or similar.

Accordingly, all indices calculated from the aforesaid $\beta_{t,x}(\lambda)$, i.e., CIE whiteness or other standards of whiteness or color values, can be matched to values under standard D65 illumination. Thus, fluorescent sample 1 can be measured with greater precision. Furthermore, measurement time is reduced because there is no need to adjust the UV cut filter 43.

FIG. 2 describes the synthesized light source of first light source 3 and second light source 4. FIG. 2(a) shows the spectral intensity $R1(\lambda)$ of first light source 3, and FIG. 2(b) shows the spectral intensity $R2(\lambda)$ of second light source 4, and these have simple spectral intensities to facilitate discussion. FIG. 2(c) shows spectral intensity $a_1(\lambda) \cdot R_1(\lambda) + a_2(\lambda) \cdot R_2(\lambda)$ of the synthesized light source when $a_1(\lambda) \leq 1$, and $0 \leq a_2(\lambda)$. FIG. 2(d) shows spectral intensity $a_1(\lambda) \cdot R_1(\lambda) + a_2(\lambda) \cdot R_2(\lambda)$ of the synthesized light source when $a_1(\lambda) > 1$, and $a_2(\lambda) < 0$. In FIGS. 2(c) and 2(d), $a_1(\lambda) + a_2(\lambda) = 1$.

Figure 2A:
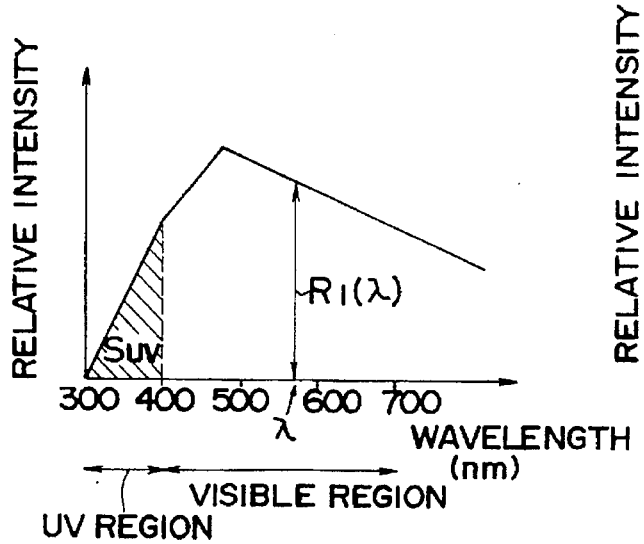
FIG. 2(a) shows the synthesis state of a light source in an embodiment of the present invention.
Figure 2B:
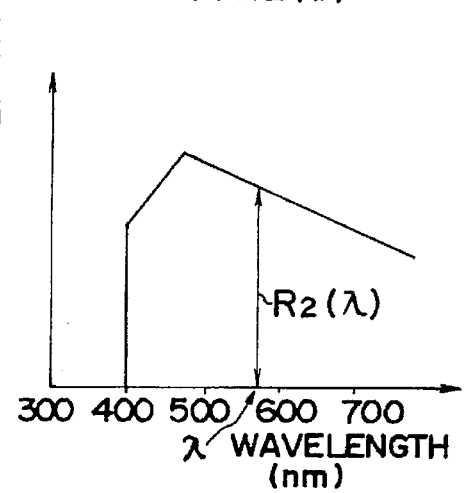
FIG. 2(b) shows the synthesis state of a light source in an embodiment of the present invention.
Figure 2C:
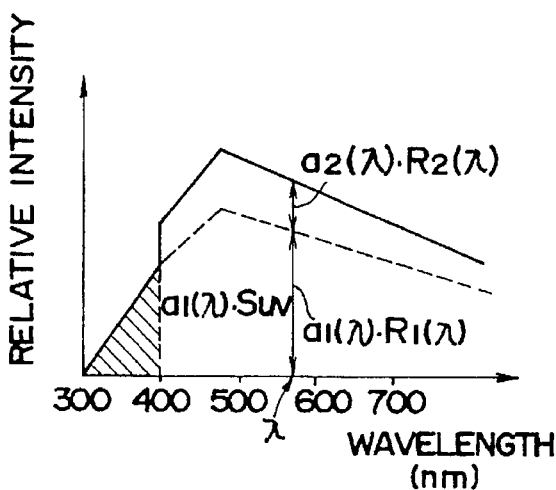
FIG. 2(c) shows the synthesis state of a light source in an embodiment of the present invention.
Figure 2D:
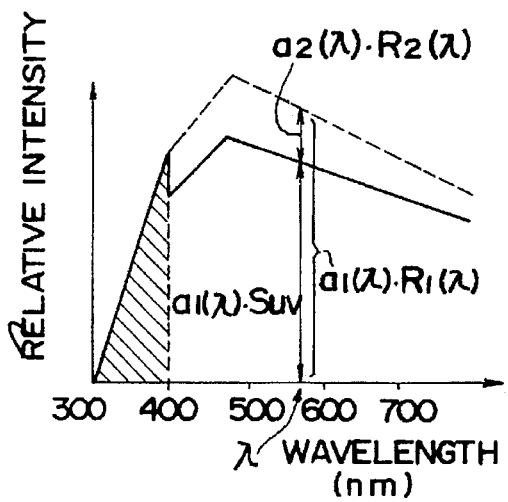
FIG. 2(d) shows the synthesis state of a light source in an embodiment of the present invention.

The ratio of the UV total spectral intensity relative to the spectral intensity in the visible range wavelength $(\lambda)$ of the synthesized light source of FIG. 2(c) is less than the value when the first light source 3 is used alone, as shown in Eq. 10. Furthermore, the ratio of the UV total spectral intensity relative to the spectral intensity in the visible range wavelength $(\lambda)$ of the synthesized light source of FIG. 2(d) is greater than the value when the first light source 3 is used alone, as shown in Eq. 11.

$$\frac{a_1(\lambda) \cdot S_{uv}}{a_1(\lambda) \cdot R_1(\lambda) + a_2(\lambda) \cdot R_2(\lambda)} \leq \frac{S_{uv}}{R_1(\lambda)} \qquad \text{Eq. 10}$$

$$\frac{a_1(\lambda) \cdot S_{uv}}{a_1(\lambda) \cdot R_1(\lambda) + a_2(\lambda) \cdot R_2(\lambda)} > \frac{S_{uv}}{R_1(\lambda)} \qquad \text{Eq. 11}$$

In Eq. 10 and Eq. 11, $S_{UV}$ refers to the spectral intensity of the total UV component when the spectral intensity area is a wavelength under 400 nm.

According to the first embodiment, the synthesized light source can control the ratio of the spectral intensity of the total UV component relative to the spectral intensity at the visible range of wavelength $\lambda$ at optional values by using first light source 3 and second light source 4 and weighting coefficients $a_1(\lambda)$ and $a_2(\lambda)$.

In the UV intensity correction of the present embodiment, $a_1(\lambda)$ and $a_2(\lambda)$ may be $a_1$ and $a_2$ (where $a_1 + a_2 = 1$) independent of wavelength. In this case, a standard fluorescent sample is measured which has known one index of CIE whiteness under standard D65 illumination, and values $a_1$ and $a_2$ are calculated so as to match values of CIE whiteness calculated from the obtained total spectral radiance factor $\beta_{t,x}(\lambda)$ to the known index. Thus, measurement time is reduced because there is not need to adjust the UV cut filter 43, and measurement operation performance is likewise improved.

If combination of $a_1$ and $a_2$ are calculated not only for standard D65 illumination but for a plurality of light sources, effectiveness is increased when evaluating a single fluorescent sample by means of a plurality of evaluation light sources.

FIG. 3 shows the construction of a second embodiment of the spectrophotometer of the present invention.

In the second embodiment, a single light source unit 9 is substituted for the first light source unit 3 and second light source unit 4 of the first embodiment. Light source unit 9 comprises a lamp 91, emitting circuit 92, UV cut filter 93, and driving unit 94. Lamp 91 emits a light flux containing a UV component such as a xenon lamp or the like, and is disposed at light source aperture 25 of integrating sphere 2. Emitting circuit 92 is pulse actuated and drives lamp 91, such that pulse light flux 95 passes through aperture 25 into integrating sphere 2.

UV cut filter 93 blocks the UV component at a wavelength of, for example, less than 400 nm, and is movably positioned between an insertion position between aperture 25 and lamp 91 and a retracted position removed from between aperture 25 and lamp 91. Driving unit 94 moves the UV cut filter 93 between the insertion position and the retracted position.

When UV cut filter 93 is at the insertion position, the light flux 95 with the eliminated UV component enters integrating sphere 2, whereas when the UV cut filter 93 is at the retracted position, light flux 95 containing a UV component enters integrating sphere 2.

Thus, light source 9 can act as a first light source 3 in the first embodiment when in the retracted position, and can act as the second light source 4 in the first embodiment when in the insertion position.

Calculation and control unit 7 moves the UV cut filter 93 between the insertion position and the retracted position by controlling driving unit 94, and controls the pulse generation of lamp 91 at said positions by controlling the actuation of emitting circuit 92, such that in these states radiant light 11 and monitor light flux 62 are obtained in illumination light containing a UV component and illumination light which does not contain a UV component.

Measurement of fluorescent sample 1 is accomplished in the same sequence as in the first embodiment. Thus, effectiveness is identical to that of the first embodiment.

In the second embodiment, a single light source 9 is used, such that excellent diffusion light is formed within integrating sphere 2 due to the lesser number of light source apertures provided in integrating sphere 2 compared to the first embodiment. Measurement precision is improved accordingly. Furthermore, the number of components around integrating sphere 2 can be reduced so as to realize a spectrophotometer of simpler construction. In this case, the use of a single light source allows the value $S_{W}'(\lambda)/R_{W}'(\lambda)$ to be substituted for $S_{W1}(\lambda)/R_{W1}(\lambda)$.

Although the UV component is completely eliminated from the second light source 4 in the first embodiment, and from the light source 9 in the second embodiment when said light source 9 acts as the second light source 4, the present invention is not limited to such an arrangement inasmuch as, for example, UV cut filters 43 and 93 may be shifted somewhat so as to allow passage of some degree of UV component to achieve an effectiveness similar to that when two light sources have different ratios of UV components.

What is claimed is:

1. A measuring apparatus for measuring an optical property of a sample comprising:
    a first light source for irradiating the sample with a light including ultraviolet rays;
    a second light source for irradiating the sample with a light not including ultraviolet rays;
    a light receiving element for receiving a light from the sample irradiated by said first or second light source;
    a first memory for storing a first output of said light receiving element at irradiation of said first light source;
    a second memory for storing a second output of said light receiving element at irradiation of said second light source;
    a means for generating weighting coefficients which weight the first output and second output of said light receiving element respectively; and
    a calculator for calculating an optical property of the sample based on the first and second output stored in said first and second memory and the weighting coefficients generated by said generating means.

2. A measuring apparatus according to claim 1, wherein said measuring apparatus measures an optical property of a fluorescent sample.

3. A measuring apparatus according to claim 2, wherein said measuring apparatus measures a fluorescent standard sample and a nonfluorescent standard sample, whose optical properties are known, before measuring a measurement sample and said generating means generates weighting coefficients based on the known optical properties and the measured optical properties of said fluorescent and nonfluorescent standard sample.

4. A measuring apparatus according to claim 1, further comprising a spectroscope for dispersing the light from the sample into multiple basic wavelength components, wherein said optical property of the sample calculated by said calculator is a spectral property.

5. A measuring apparatus according to claim 4, wherein said generating means generates weighting coefficients corresponding to each of the multiple basic wavelength components.

6. A measuring apparatus according to claim 1, further comprising:
    another light receiving element for receiving the light from said first or second light source;
    a third memory for storing a third output of said another light receiving element at irradiation of said first light source; and
    a fourth memory for storing a fourth output of said another light receiving element at irradiation of said second light source; wherein
    said calculator calculates the optical property of the sample based on the first, second, third, and fourth output stored in said first, second, third, and fourth memory and the weighting coefficients generated by said generating means.

7. A measuring apparatus according to claim 1, further comprising a controller for causing said first and second light sources to irradiate the sample in sequence.

8. A measuring apparatus according to claim 1, wherein said second light source has a UV cut filter for intercepting the ultraviolet rays.

9. A measuring apparatus for measuring an optical property of a sample comprising:
    a light source for irradiating the sample with a light including ultraviolet rays;
    UV cut member, movable between a first position and a second position, for cutting off the ultraviolet rays, wherein said UV cut member allows the ultraviolet rays of said light source to irradiate the sample at the first position and prevents the ultraviolet rays from irradiating the sample at the second position;
    a light receiving element for receiving a light from the sample irradiated by said light source;
    a controller for causing said light source to irradiate the sample with said UV cut member at the first position and at the second position;
    a first memory for storing a first output of said light receiving element at irradiation of said light source with said UV cut member at the first position;
    a second memory for storing a second output of said light receiving element at irradiation of said light source with said UV cut member at the second position;
    a means for generating weighting coefficients which weight the first output and second output of said light receiving element respectively; and
    a calculator for calculating an optical property of the sample based on the first and second output stored in said first and second memory and the weighting coefficients generated by said generating means.

10. A measuring apparatus according to claim 9, wherein said measuring apparatus measures an optical property of a fluorescent sample.

11. A measuring apparatus according to claim 10, wherein said measuring apparatus measures a fluorescent standard sample and a nonfluorescent standard sample, whose optical properties are known, before measuring a measurement sample and said generating means generates weighting coefficients based on the known optical properties and the measured optical properties of said fluorescent and nonfluorescent standard sample.

12. A measuring apparatus according to claim 9, further comprising a spectroscope for dispersing the light from the sample into multiple basic wavelength components, wherein said optical property of the sample calculated by said calculator is a spectral property.

13. A measuring apparatus according to claim 12, wherein said generating means generates weighting coefficients corresponding to each of the multiple basic wavelength components.

14. A measuring apparatus according to claim 9, further comprising: another light receiving element for receiving the light from said light source;
   a third memory for storing a third output of said another light receiving element at irradiation of said light source with said UV cut member at the first position; and
   a fourth memory for storing a fourth output of said another light receiving element at irradiation of said light source with said UV cut member at the second position; wherein said calculator calculates the optical property of the sample based on the first, second, third, and fourth output stored in said first, second, third, and fourth memory and the weighting coefficients generated by said generating means.

15. A measuring apparatus according to claim 9, wherein said UV cut member cuts off a light whose wavelength is less than 400 nm.

16. A method for measuring an optical property of a sample, said method comprising the steps of:
   irradiating the sample with a first light including ultraviolet rays;
   receiving a light from the sample irradiated by the first light and outputting a first signal corresponding to the received light;
   irradiating the sample with a second light, wherein the ratio of ultraviolet rays of the second light is different from that of said first light;
   receiving a light from the sample irradiated by the second light and outputting a second signal corresponding to the received light;
   generating weighting coefficients which weight the first signal and second signal respectively; and
   calculating an optical property of the sample based on the first and second signal and the weighting coefficients.

17. A method according to claim 16, wherein said method is for measuring an optical property of a fluorescent sample.

18. A method according to claim 17, further comprising the steps of:
   measuring a fluorescent standard sample whose optical properties are known;
   measuring a nonfluorescent standard sample whose optical properties are known; and
   calculating the weighting coefficients based on the known optical properties and the measured optical properties of said fluorescent and nonfluorescent standard sample.

19. A method according to claim 16, further comprising the steps of:
   dispersing the light from the sample into multiple basic wavelength components;
   receiving the dispersed light and outputting signals corresponding to the received light of the multiple basic wavelength components; and
   calculating a spectral property of the sample based on the output signals corresponding to the multiple basic wavelength components.

20. A method according to claim 19, wherein said generating step includes the step of generating weighting coefficients corresponding to each of the multiple basic wavelength components.

21. A method according to claim 16, wherein said second light irradiating step includes the step of providing a UV cut member for cutting off the ultraviolet rays.

22. A measuring apparatus for measuring a total spectral radiant factor of a fluorescent sample comprising:
   a first light source for irradiating the sample with a light including ultraviolet rays;
   a second light source for irradiating the sample with a light not including ultraviolet rays;
   a first measuring device for measuring a spectral luminous intensity of a light radiated from the sample irradiated by said first and second light source;
   a second measuring device for measuring a spectral luminous intensity of a light from the first and second light source;
   a controller for controlling said first and second measuring device so as to measure a nonfluorescent white standard sample, whose spectral luminous intensity is known, and to measure a measurement sample in sequence;
   a generating means for generating weighting coefficients which weight each of the spectral luminous intensities measured by said first and second measuring device;
   a calculator for calculating a total spectral radiant factor $\beta_{t,x}(\lambda)$ of the sample as follows:

$$\beta_{t,x}(\lambda) = W(\lambda) \frac{S'(\lambda)}{R'(\lambda)} / \frac{Sw'(\lambda)}{Rw'(\lambda)}$$

$$S'(\lambda) = a1(\lambda) \cdot S1(\lambda) + a2(\lambda) \cdot S2(\lambda)$$

$$R'(\lambda) = a1(\lambda) \cdot R1(\lambda) + a2(\lambda) \cdot R2(\lambda)$$

$$Sw'(\lambda) = a1(\lambda) \cdot Sw1(\lambda) + a2(\lambda) \cdot Sw2(\lambda)$$

$$Rw'(\lambda) = a1(\lambda) \cdot Rw1(\lambda) + a2(\lambda) \cdot Rw2(\lambda)$$

where
   $W(\lambda)$: known spectral luminous intensity of the nonfluorescent white standard sample;
   $S1(\lambda)$: measured spectral luminous intensity of the sample irradiated by said first light source;
   $S2(\lambda)$: measured spectral luminous intensity of the sample irradiated by said second light source;
   $R1(\lambda)$: measured spectral luminous intensity of the first light source at the sample measurement;
   $R2(\lambda)$: measured spectral luminous intensity of the second light source at the sample measurement;
   $Sw1(\lambda)$: measured spectral luminous intensity of the nonfluorescent white standard sample irradiated by said first light source;
   $Sw2(\lambda)$: measured spectral luminous intensity of the nonfluorescent white standard sample irradiated by said second light source;
   $Rw1(\lambda)$: measured spectral luminous intensity of the first light source at the nonfluorescent white standard sample measurement;
   $Rw2(\lambda)$: measured spectral luminous intensity of the second light source at the nonfluorescent white standard sample measurement; and
   $a1(\lambda)$, $a2(\lambda)$: weighting coefficients.

23. A measuring apparatus for measuring an optical property of a sample comprising:
   a first light source for irradiating the sample with a first light including ultraviolet rays;
   a second light source for irradiating the sample with a second light, wherein the ratio of ultraviolet rays of the second light is different from that of said first light; and a calculator for calculating weighting coefficients which synthesize a composite light source from said first and second light source, wherein a measurement value under illumination of the composite light source matches to a measurement value under illumination of a standard light source.

* * * * *